(12) United States Patent
Defemme et al.

(10) Patent No.: US 11,116,694 B2
(45) Date of Patent: Sep. 14, 2021

(54) DEVICE FOR DISPENSING LIQUID FROM A STERILE PACKAGING BOTTLE

(71) Applicant: Laboratoires Thea, Clermont-Ferrand (FR)

(72) Inventors: Alain Defemme, Chamalieres (FR); Fabrice Mercier, Clermont-Ferrand (FR)

(73) Assignee: LABORATORIES THEA, Clermont-Ferrand (FR)

(*) Notice: Subject to any disclaimer, the term of this patent is extended or adjusted under 35 U.S.C. 154(b) by 808 days.

(21) Appl. No.: 15/562,914

(22) PCT Filed: Mar. 31, 2016

(86) PCT No.: PCT/IB2016/000408
§ 371 (c)(1),
(2) Date: Sep. 29, 2017

(87) PCT Pub. No.: WO2016/156968
PCT Pub. Date: Oct. 6, 2016

(65) Prior Publication Data
US 2018/0078455 A1    Mar. 22, 2018

(30) Foreign Application Priority Data
Mar. 31, 2015   (WO) ................. PCT/IB2015/000423

(51) Int. Cl.
*A61J 1/14*     (2006.01)
*B65D 47/18*    (2006.01)
(Continued)

(52) U.S. Cl.
CPC .............. *A61J 1/145* (2015.05); *A01N 59/16* (2013.01); *A61J 1/1456* (2015.05);
(Continued)

(58) Field of Classification Search
CPC ........ A61J 1/1443; A61J 1/145; A61J 1/1456; A61F 9/0008
See application file for complete search history.

(56) References Cited

U.S. PATENT DOCUMENTS 5,496,471 A * 3/1996 Heyl ..................... A61F 9/0008
 210/266
5,681,468 A    10/1997 Sawan et al.
(Continued)

FOREIGN PATENT DOCUMENTS

WO   2006/000897 A1   1/2006
WO   2011/095877 A1   8/2011

OTHER PUBLICATIONS

International Search Report dated Jul. 12, 2016 issued in corresponding PCT/IB2016/000408 application (2 pages).

*Primary Examiner* — Tatyana Zalukaeva
*Assistant Examiner* — Jessica R Arble
(74) *Attorney, Agent, or Firm* — Millen, White, Zelano & Branigan, P.C.

(57) ABSTRACT

The invention relates to a device for dispensing an aqueous liquid through an interface membrane made partially hydrophilic and partially hydrophobic, made so that when in operation, during each operation of dispensing a metered amount of liquid, the streams of air and liquid flow alternately in a capillary channel (18) downstream from the membrane. Said interface membrane (7) is made of a filtering material which includes biocidal metal cations in the body thereof. Said device comprises a porous insert (8), which is permeable both to liquid and to air, which is arranged upstream from the membrane in the path of the fluids and which is made of a material including sites with negative charges capable of attracting biocidal metal cations from said membrane.

17 Claims, 2 Drawing Sheets

(51) Int. Cl.
    *A01N 59/16*     (2006.01)
    *B01D 61/14*     (2006.01)
    *B01D 67/00*     (2006.01)
    *B01D 69/02*     (2006.01)
    *B01D 71/02*     (2006.01)
    *B65D 35/14*     (2006.01)

(52) U.S. Cl.
    CPC ....... *B01D 61/147* (2013.01); *B01D 67/0044* (2013.01); *B01D 69/02* (2013.01); *B01D 71/022* (2013.01); *B01D 71/028* (2013.01); *B65D 35/14* (2013.01); *B65D 47/18* (2013.01); *B01D 2311/2692* (2013.01); *B01D 2323/30* (2013.01); *B01D 2325/36* (2013.01); *B01D 2325/38* (2013.01)

(56) References Cited

U.S. PATENT DOCUMENTS

| | | | |
|---|---|---|---|
| 7,971,755 B2 | 7/2011 | Faurie | |
| 9,174,777 B2 | 11/2015 | Defemme et al. | |
| 2008/0067194 A1 | 3/2008 | Faurie | |
| 2011/0212326 A1* | 9/2011 | Ettrich ................. | C09D 175/04 428/335 |
| 2012/0310185 A1* | 12/2012 | Defemme .............. | B65D 47/18 604/296 |
| 2013/0264277 A1* | 10/2013 | Heidenreich ........... | C02F 1/001 210/508 |
| 2014/0356767 A1* | 12/2014 | Kimura ................. | D06M 11/83 429/532 |

\* cited by examiner

DEVICE FOR DISPENSING LIQUID FROM A STERILE PACKAGING BOTTLE

The invention relates to devices for dispensing liquid that are used in the techniques for the manufacture of small bottles for packaging products that must be stored in a sterile condition, not only until the bottle is opened, but subsequently throughout consumption of the product, until the entire contents of the bottle have been used.

A typical example of the requirements that the invention aims to satisfy is in the field of multi-dose bottles accommodating aqueous solutions to be dispensed discontinuously, in doses that are spaced out over time, which are equipped with air/liquid interface membranes that obstruct the passage of microbiological contaminants from the ambient air into the bottle by the effect of filtration.

Such membranes are also known that have in addition the feature of being doubly selectively permeable, preferentially allowing either air or liquid to pass through, depending on a pressure difference prevailing between their two faces, in the upstream-to-downstream direction during the phase of expulsion of a dose of liquid from the bottle and, alternately, in the downstream-to-upstream direction during the aspiration phase when air is required to enter the bottle to compensate for the volume extracted therefrom. In the Applicant's existing patents a description is given of how such membranes, called bi-functional membranes (bi-functional from the point of view of transports of liquid or gaseous flows), are used to ensure an alternate circulation of liquid and air through a capillary channel for the expulsion of the liquid arranged after the membrane. Such membranes acting as an interface between the closed space of a sterile packaging bottle for an aqueous liquid (an aqueous solution of a pharmaceutically active ingredient in particular) are produced partially from a hydrophilic material, over a first zone of the total extent of the interface, and partially from a hydrophobic material, over a second zone of the same extent. The functioning of a membrane produced in this way is described in particular in the published French patent application numbered FR 2872137 (corresponding international application WO 2006000897), for a membrane arranged across a single duct allowing the passage of the flows of air and of liquid in one direction and in the other between the inside and outside of a bottle with an elastically deformable wall manipulated in order to produce alternate expulsion and aspiration.

In such a context, the invention aims to provide a liquid dispensing device with microbiological protection, offering a high level of safety in respect of both microbial sterility and chemical toxicity in its application to packaging bottles for sterile liquid products for which sterility must be maintained throughout the consumption of the contents of the bottle, during successive dispensing operations that are spaced out over time. One major objective that it is sought to achieve thereby is to enable progressive consumption over long periods, another being to allow a multidose packaging for pharmaceutical or parapharmaceutical products that are applied on highly contaminated sites.

With these objectives in view, the invention proposes to utilize a hydrophilic-hydrophobic bi-functional membrane the mass of which is also loaded with a biocidal agent acting by the ionic oxidation effect. Such an agent is supplied more particularly by macromolecules bearing positively-charged metal ions, such as those proposed by now well-known prior art in the form of mineral polymers of the amino-silicate family, called zeolites, retaining within them labile metal cations. Among the useful ions are silver ions (Ag+ or Ag++) which have been found to be the most advantageous in an industrial context for antibacterial protective membranes utilized according to the present invention.

In a liquid dispenser according to the invention, such a membrane is used as a permanent source of biocidal metal ions in combination with a porous mass interposed in the path of the fluids upstream of the membrane, the mass being constituted so as to be capable of retaining within it the biocidal ions that reach it having been extracted from the membrane during the aspiration phase at each operation of dispensing a dose of liquid, thus constituting a secondary reserve of active ions, while at the same time forming, with respect to the transport of these ions, a plug that prevents them from reaching the space accommodating the liquid inside the bottle. In practice, it has been observed that the ions thus placed in reserve, when not consumed in situ, are easily released and entrained back towards the membrane during the expulsion phase of a subsequent dispensing operation.

Membranes at the water/air interface loaded with biocidal metal cations have been known for a very long time, as demonstrated for example by the American patent U.S. Pat. No. 5,681,468, filed in 1993 and published in 1997. However, it had never been envisaged that biocidal cations could act otherwise than by attacking the bacteria contaminating the expelled liquid when it is situated downstream of the membrane having passed therethrough. Nor had it ever been proposed to mount the membrane as envisaged by the invention, in a device combining the membrane with a porous mass for retaining the same active ions with which the membrane is loaded, as well as means for organizing the circulation of the fluids through them, providing alternation of the flows at the level of the membrane and in the zone downstream of the device.

In the practical implementation of the invention, this porous mass is designed in the form of an insert mounted in the device for dispensing liquid, upstream of the membrane, as a non-sealing closure stopper of the connecting duct between the inside and the outside of the bottle. By virtue of its porosity and its arrangement, the insert is then advantageously designed so as to act as the flow regulator plugs that are known from the ophthalmic dropper bottles described in the Applicant's earlier patents, thanks to the fact that they impose a pressure loss on the path of the liquid pushed out of the bottle.

On the other hand, in order for such an insert to contribute to protection against pollutants affecting sterility as provided according to the present invention, it is specially made of a polymeric material having active, negatively-charged sites, thereby capable of attracting the biocidal metal cations with which the membrane is initially loaded. Preferred materials from this point of view are constituted by polymers based on polyolefins copolymerized with compounds having a carboxylic acid function. According to the relative proportions of the constituents, and according to the conditions under which the copolymerization reactions take place, a significant proportion of free carboxyl sites remain in the polymer obtained, ready to bind with the cations used as biocidal cations that come into contact with the polymer.

According to a preferred embodiment of the invention, the specific capacity of the polymeric material for retaining metal cations can be increased by subjecting the polymer to an irradiation treatment having the effect of releasing other carboxyl groups.

The overall mode of operation of the device according to the invention will be detailed in the remainder of the present description, with reference to the case in which it equips a flexible-walled sterile packaging bottle for an ophthalmic solution, which can be elastically deformed by compression of the volume of the internal reservoir. It must however be understood that other means can make it possible similarly to ensure the pressure variations causing, at each operation of dispensing a dose of liquid, firstly a phase of propulsion from the inside to the outside of the bottle and expulsion of the liquid beyond the capillary channel situated downstream of the membrane, then an aspiration phase, causing outside air to enter the bottle, the air then being preceded by a back flow of liquid that has not been expelled. In particular, it is possible to envisage a bottle with an axially mobile base meeting an elastic return means or a bottle equipped with a pump system. On the other hand, reference will be made preferentially to a drop-dispensing device, but it must be understood that the device according to the invention can be adapted to dispensing individual doses that are larger than drops, as well as to an outlet of the capillary channel dispensing the liquid in other forms, for example in the form of a jet or with spatial diffusion.

Initially, throughout the entire duration of storage preceding first use, the bottle remains hermetically sealed over a head of pressurized sterile air surmounting the space accommodating the liquid, so that the membrane remains dry. It will only become soaked with liquid in its hydrophilic zone the first time liquid is expelled after the bottle is opened.

The downstream space of said device comprises a capillary channel in which liquid flow and gaseous flow circulate alternately, without ever mixing, so that during operation, when said channel has finished conveying the flow of liquid to be expelled to the outside, a non-expelled remainder of liquid is left, that occupies said channel temporarily. This remainder is recycled as back flow through the membrane under the pressure of the flow of air aspirated from the outside when the pressure difference between the two faces of the membrane ceases to be exerted in the direction of expulsion. In this aspiration phase, the back flow of liquid passes through the hydrophilic zone of the membrane, while the inflow of air compensating for the volume of liquid dispensed passes through the hydrophobic zone.

Upstream of the membrane, the space arranged in the device according to the invention forms a duct which, unlike the downstream capillary channel, has a large cross-section. Arranged in this duct is the porous insert providing negative charges in the reactions that tend to retain the biocidal metal ions conveyed by the liquid in chemical bonds of loads with the polymer of the insert at the level of the active sites which it presents in particular in the form of free carboxyl groups. This insert, also called a plug, is situated there in the presence of the flows both of liquid and of air, which together come into contact with the polymer of which it is constituted in the cells of the porous material. The contact takes place over a large surface area, corresponding to the specific surface of the porous material. When the device is in operation, the porous insert retains the biocidal metal cations sufficiently so that the liquid in reserve in the bottle cannot be chemically contaminated by biocidal cations. On the other hand, it ensures that to-and-fro movements of biocidal cations are established, conveyed by the flows and back flows of liquid, in particular in outward and return directions between the membrane and the porous insert, according to a phenomenon that favours a high level of biocidal activity in said device for dispensing liquid, while protecting the liquid in reserve from microbiological contamination.

In fact, surprisingly, the inventors have demonstrated that said device according to the invention retains a high level of biocidal activity throughout the entire duration of its use for discontinuous dispensing of liquid. As will be detailed hereinafter, it has been shown that the dispensing device according to the invention used mounted in a sealed manner as closure of a bottle in order to produce a multidose bottle, containing for example sterile eye drops, is very effective in terms of sterility throughout the consumption of the eye drops. Consumption of the contents can thus be spaced out over a much longer time than with existing bottles, with complete safety as regards absence of risk to the patient.

The inflow of air compensating for the expelled liquid, which originates from ambient air loaded with microorganisms, is sterilized mainly during its passage through the membrane by biocidal action of contact with the biocidal cations in the pores of the membrane in its hydrophobic part, and if appropriate by antibacterial filtration. In addition, if necessary, due to the fact that biocidal cations conveyed by the back flow of the remaining non-expelled liquid are retained in the insert at the end of each dispensing of liquid, there is always some active biocidal agent available to destroy the microorganisms from the stagnant air inside said insert mixed with a portion of remaining liquid.

Tests described hereinafter confirm that biocidal cations are progressively collected in the porous insert, following a gradient of decreasing quantity running from the end portion closest to the membrane, here called proximal, to the opposite end portion closest to the reserve of liquid, here known as distal, such that the reserve of liquid remains free of biocidal cations.

Moreover, after the first operation of said device for dispensing liquid, said porous insert that becomes loaded with biocidal cations then forms a source of biocidal cations that can be partially extracted during the passage of the liquid flow leaving the inside of the bottle through said insert, to join available sites on the membrane.

Thus a to-and-fro movement of biocidal cations is created in the fluid circulation duct associated with the to-and-fro movement of the liquid, which maintains a relatively stable quantity, during uses, of the biocidal cations available within the device according to the invention, to be active on the microorganisms coming into contact with them.

In principle, the invention thus appears to consist of producing the bi-functional water/air interface membrane on the one hand and the plug insert installed as a non-sealing stopper of the bottle on the other hand, in such a way that in operation, after the bottle is opened for a first use for dispensing liquid, the membrane and the insert work together in order to create between them a bed of mobile ions that are removed from the insert by the flow of liquid extracted from the bottle at each dispensing operation (during the liquid-expulsion phase) from those which have been brought there by a back flow of liquid not dispensed during previous operations of dispensing liquid (during the air-aspiration phase).

Overall, the quantity of biocidal metal ions which is effectively consumed in destruction of biological contaminants is admittedly very low with respect to that which is displaced at each operation, which is itself very low with respect to the initial capacity of the membrane. The quantity consumed depends on the degree of contamination of the aspired ambient air for effective treatment of the air, the efficiency of which will improve as the surface area of contact with the loaded materials increases. The quantity displaced results from the flow of liquid entraining the active cationic load, or more precisely the mass of liquid displaced at each back flow of liquid from the membrane to the insert and each direct flow to the membrane on expulsion.

With these considerations in mind, it is possible to adapt the device for dispensing liquid according to the invention to applications in more or less contaminating environments, even in harsh conditions in terms of the overall volume of solution to be dispensed, the total duration of use of the bottle and the frequency of repetition of the dispensing operations, by adjusting the respective shapes and dimensions of the membrane and of the porous insert, assuming that the materials constituting each of them remain unchanged.

With respect to the membrane itself, the present invention advantageously provides for it to be made of a hydrophilic porous polymeric material homogenously loaded with an agent having a biocidal effect by ionic oxidation, said material constituting said membrane throughout its entire mass and then being rendered hydrophobic locally over a of the extent of the membrane installed across the circulation duct of the fluids between inside and outside of the bottle, by an additional polymerization treatment protecting its biocidal activity.

This makes it possible to arrange a suitable volume for placing the gaseous phase, constituted by air, in contact with the polymeric material loaded with active ions with biocidal effect within the porous mass over the entire thickness of the membrane. The same purpose is served by the fact that the hydrophilic base material of the membrane is constituted in a finely homogeneous manner, which excludes earlier realizations of filter membranes made of a filament-based material retaining charged particles between the fibres. According to the invention, it is preferred to start from a molten polymer base comprising fusible granules of a masterbatch, itself incorporating mineral macromolecules bearing active ions with a biocidal effect.

Whereas conventionally, filtration of the bacteria requires a fine porosity, not exceeding 0.2 µm, the presence of a biocidal agent within the membrane makes it possible to maintain sterility satisfactorily with coarser porosities, preferentially of around 0.3 or 0.4 µm, or more generally up to 0.5 µm, or even up to 0.6 or 0.8 µm, or even 1 µm, which is advantageous from the point of view of pressure losses and allows viscous liquid to be treated. In practice, the invention also makes provision, in a preferred embodiment, for producing the membrane such that it has an average pore diameter adapted for filtering out microorganisms having dimensions greater than a particle size comprised between 0.3 and 1 µm, in particular between 0.3 and 0.6 micrometre. In total, the porosity of the membrane could thus be adjusted to any value between 0.1 and 1 micrometre depending on the physico-chemical properties of the liquid.

The support macromolecules of the biocidal ions are advantageously, as has already been indicated, mineral polymers of the aluminosilicates type, in which the biocidal ions are incorporated, more specifically, in a manner known per se, being metal ions such as silver ions or similar metals in ionic form, which bind to the free sites of the polysiloxane chains via polar covalent bonds. These mineral polymers are preferably crystalline polymers. Without restricting the conditions of application of the invention, the active ions concentration in the membrane is preferably chosen comprised between 100 and 100,000 ppm, taking as an example the case of a mineral polymer based on aluminosilicates bearing silver ions in a membrane with a porosity of approximately 0.2-0.3 micrometre with an effective extent of the order of 3 cm$^2$.

Among the metal ions useful to the invention, copper or zinc ions may be retained, but silver ions have been found to be the most advantageous in the industrial context of the microbial protection device utilized according to the present invention.

As a secondary feature, the invention extends beyond the liquid-dispensing device according to the invention, to a sterile packaging bottle making use thereof, to be utilized in particular within the context of the sterile packaging of pharmaceutical or parapharmaceutical products.

The invention also relates to a particular process for the manufacture of the membrane itself.

Advantageously, means for organizing the circulation of the fluids complete the dispensing device mounted on a packaging bottle. Preferentially, said packaging bottle has a wall that is reversibly elastically deformed, in order to ensure the entry of outside air compensating for any dose of liquid expelled from the bottle as well as the back flow returning through said device of any non-expelled remaining liquid, said membrane being mounted with said porous insert in said device for dispensing liquid in combination with means for organizing the circulation of the air and liquid fluids therethrough, and in which said membrane is arranged at the base of a dropper tip comprising the capillary channel for the expulsion of the drops, opposite a base of said tip in which are arranged respective means of guiding the air aspired from the outside and any remaining liquid that has not been dispensed and is required to flow back through the membrane from the downstream space to the upstream space, said means tending to direct the airflow to the hydrophobic part of the membrane preferably arranged in the centre of said membrane and to distribute the liquid over its hydrophilic part.

DESCRIPTION OF AN EMBODIMENT OF A BOTTLE

The invention will now be described more fully within the context of preferred features and their advantages, according to non-limitative examples, with reference to a device according to the invention for dispensing a sterile liquid in its application to the maintenance of sterility in a bottle with a dropper tip as illustrated in FIGS. 1 to 4.

Figure 1:
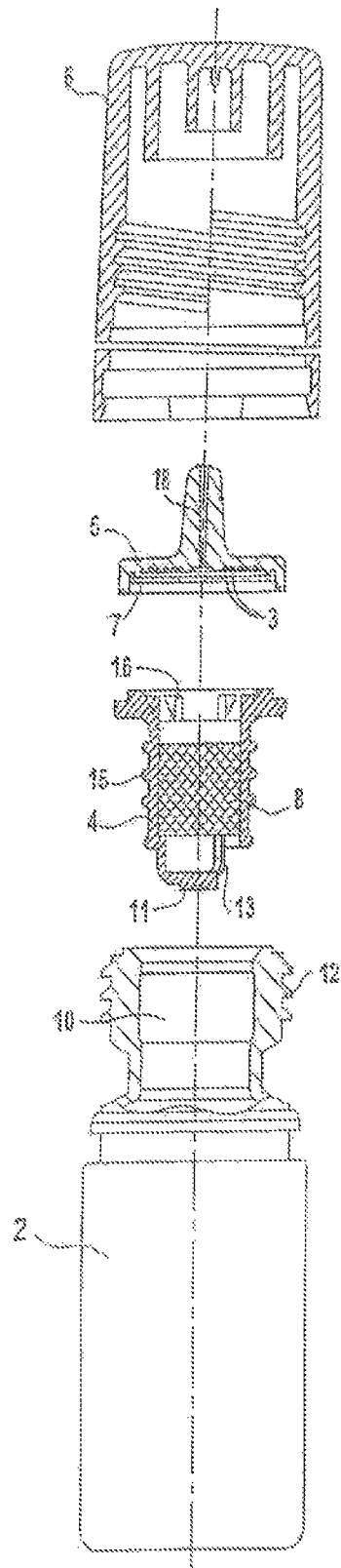
FIG. 1 shows, in an exploded view in longitudinal section, the various elements of a bottle with a deformable wall from which a liquid is expelled in successive doses through a dispensing device for microbiological protection according to the invention.
Figure 2:
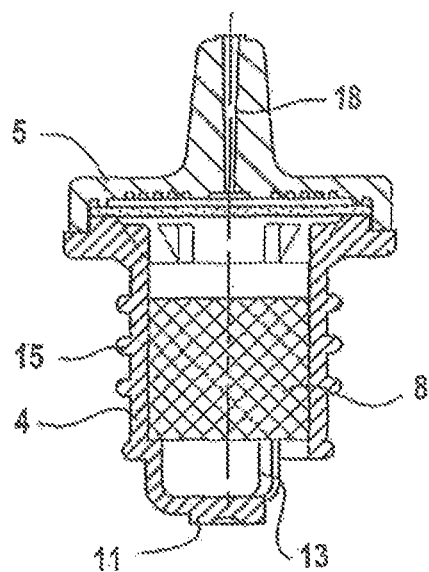
Figure 3:
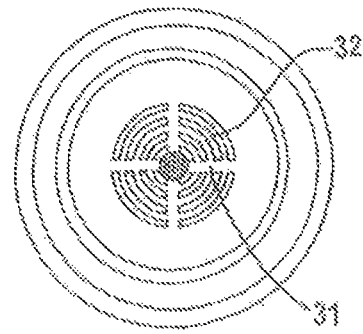
Figure 4:
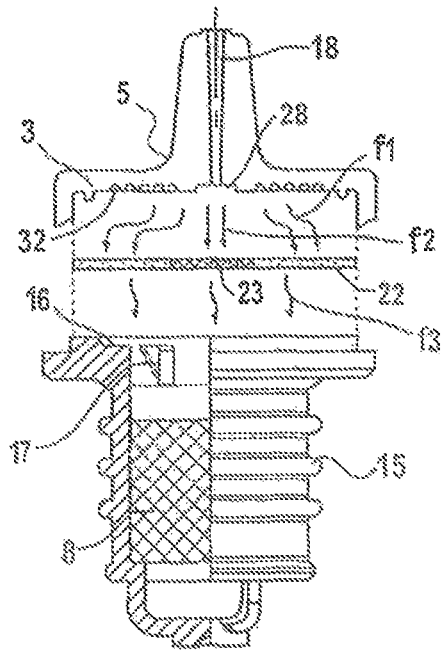

the longitudinal section of FIG. 2 shows the dispensing device more particularly, once its specific elements are assembled to constitute a head for the dispensing of liquid and entry of outside air, for insertion into the neck of the bottle;

FIG. 3 shows the configuration of the base of the tip on its surface located facing the nacelle of the device shown in FIG. 1 or 2;

FIG. 4 shows, in a partially exploded view, the circulation of the fluids returning into the circulation duct of the dispensing device according to the invention shown in FIG. 1 or 2.

In its general construction and as shown in all its elements in FIG. 1, the bottle equipped with a dispensing head appears to conform to the usual design for sterile packaging bottles. The bottle comprises a reservoir 2 accommodating the aqueous liquid to be dispensed in a sterile condition, surmounted by a dispensing device mounted in a sealing manner in the neck of the bottle 10. However, it differs therefrom by features specific to the invention that are distributed over its constituent elements, essential for dispensing, under ensured microbiological protection according to the invention, along the duct for the circulation of the aqueous liquid to be dispensed and of the air entering, compensating for the liquid expelled, namely mainly in the upstream portion of this duct, the porous insert 8 in the form of a plug occupying the internal space in the nacelle 4, and at the interface of these downstream and upstream parts of the membrane 7. It also differs therefrom in their relative assembly linked to the circulation of the fluids and to the resulting effects on the biocidal activity in the duct.

According to the invention, the selective permeability membrane that the dispensing device contains is used for separating the flows of liquid and of air that pass through it, as a microbiological protection membrane by filtration and by the fact that its material contains mineral macromolecules bearing biocidal cations, for the destruction of the bacteria or similar microorganisms conveyed in the fluids that pass through it.

In the example chosen to better illustrate the invention, the membrane is based on an organic polymer, more specifically in the present case based on polyester resin modified by a polyamide or polyethersulphone resin, into which the mineral macromulecules supporting the biocidal cations have been incorporated in the mass thereof, more particularly here a zeolite loaded with silver cations. It is hydrophilic and is rendered hydrophobic over only a part of its extent across the duct arranged in the dispensing device. For example, this is done via local exposure to irradiation under ultraviolet radiation, which modifies the structure of the polymer in situ, by radical crosslinking reactions between its constituents, while maintaining the properties of the biocidal cations of the zeolites.

The membrane shown in FIG. 4 thus has a hydrophilic zone 22 preferentially allowing the aqueous liquid to pass through it in the presence of air, and a hydrophobic zone 23 preferentially allowing air to pass through it in the presence of water or of the aqueous liquid. The ionic load with biocidal effect is present both in the hydrophobic zone and in the hydrophilic zone.

In operation, during the successive operations of dispensing the doses of liquid out of the bottle, spaced out over time, the structure of the membrane, in conjunction with the organization of the circulation through it of the fluids, tends to promote action that destroys the microorganisms and is exerted on the airflow within the hydrophobic material itself by contact between the air and the polymer loaded with ions at the surface of the pores, while conversely, in the hydrophilic part of the membrane, the biocidal ions are not consumed but entrained and conveyed further by the liquid passing through the membrane.

Inside the duct for the circulation of the fluids, upstream of the membrane 7 on the side of the closed inner space of the bottle, there is a porous insert 8, the main role of which, according to the invention, is to retain the biocidal cations brought to it by each backflow of aqueous liquid constituted by the non-expelled remainder of the dose of liquid previously drawn off from the bottle, and to allow distribution to the membrane of the biocidal cations with which it has become loaded when a new dose of liquid is subsequently expelled from the bottle.

In conventional examples within the context of ophthalmic applications, the length of the porous insert along the axis of the bottle is 9 mm and the diameter 9.6 mm. More generally, and by way of indication, the length of said insert can be comprised between 5 and 15 mm. The dimensions of the insert are adapted to the size of its receptacle.

Its distance from the upper face of the membrane in question is of the same order of magnitude. Its porosity corresponds to an air flow rate of 3,000 ml/mn, as measured according to the "water flow" capacitive method, consisting of measuring the time taken to fill a given volume using a chronometer. Its volumetric mass density according to the example is of the order of 0.50 g.cm$^3$.

More generally, the porosity of the insert, which comprises a large number of open cells, preferably corresponds to an air flow rate comprised between 1,000 and 4,000 ml/min, measured according to the "water flow" capacitive method. Its volumetric mass density is preferably comprised between 0.20 and 0.80 g.cm$^3$.

Acidity Tests of the Porous Insert

The porous insert intended for a bottle for ophthalmic liquid according to the example in question here is produced from an extruded polyethylene-based polymer filament that is subjected to compaction. The polymer comprises carboxyl groups initially to the extent that ethylene has been copolymerized with compounds having carboxylic acid functions, here constituted for example by higher homologues (with C4-C10 hydrocarbon chain) of carboxylic acid, in a proportion of 25% at most.

At this stage it already comprises carboxyl sites left free by the polymerization reactions. This explains the test results reported below that make it possible to show the relationship between the effect on the cations and the acidity measured in the insert.

The proportion of free carboxyl sites can be increased by exposing the product to a radiation capable of breaking the molecules of the polymer. Beta or gamma rays are suitable for this.

By way of example, the compacted insert is subjected, in the presence of air, to an irradiation by gamma rays (Cobalt 60 source, 25 kGy). The radicals formed in the polymeric material during the irradiation react with air in order to form carboxyl anionic groups in particular.

The content of carboxyl sites before and after irradiation is studied using acidity measurements that are carried out according to the principle of acidity or alkalinity assay from the European Pharmacopoeia 8.6 for polyolefins. These measurements are carried out by comparison with purified water, on warm water with non-irradiated inserts and on warm water with irradiated inserts.

The results are shown in Table 1 hereinafter.

TABLE 1

|  | Purified water | Non-irradiated inserts | Irradiated inserts |
| --- | --- | --- | --- |
| pH | 6.8 | 5.5 | 5.0 |
| Vh (ml) | 1.2 | 1.5 | 2.4 |

The decrease in the pH and the increase in the equivalent volume (Vh) at the end-point of the coloured indicator demonstrate the creation of a large number of acid sites in the irradiated inserts, hence a significant increase with respect to the case of the copolymer inserts with monomers having carboxylic functional groups not yet irradiated.

The remainder of liquid reaching the reservoir receiving liquid inside the bottle reaches there sterile and free of biocidal cations. The proof of this is established by the tests hereinafter.

Safety Testing for the Sterile Stored Liquid

Tests were carried out in order to determine the quantity of silver ions found in the closed space, upstream of the membrane, of a first bottle containing a solution A and a second bottle containing a solution B, solutions described below, namely in the insert cut into three sections of equal thicknesses over its length, forming the proximal portion of the insert, the central portion of the insert and the distal portion of the insert, as well as in the solution in reserve, at different times of use of the bottles that correspond to a volume of solution extracted from the bottle by intermittent expulsions of drops.

In these tests, two solutions in an aqueous medium known as eye drops are tested: a physiological solution A containing as active ingredient sodium chloride in an aqueous medium usually utilized as eye drops in the treatment of dry eye, and an ophthalmic solution B containing as active ingredient timolol maleate in an aqueous medium usually utilized as eye drops in the treatment of glaucoma.

The results are shown hereinafter in Table 2 for solution A and in Table 3 for solution B.

TABLE 2

Quantity of silver ions in upstream portion of duct for circulation of fluids for solution A

| | Time of use of the bottle | | | |
|---|---|---|---|---|
| | First use | 15 days | 30 days | 90 days |
| Volume of solution A extracted | 4 drops (0.15 ml) | 1.67 ml | 3.35 ml | 10 ml (approximately 300 drops) |
| In proximal portion of the insert (ppm) | 4.18 | 0.88 | 1.03 | 0.94 |
| In central portion of the insert (ppm) | 1.75 | 0.56 | 0.44 | 0.61 |
| In distal portion of the insert (ppm) | 0.81 | 0.26 | 0.31 | 0.22 |
| In the reservoir (ppm) | <0.001 ppm | <0.001 ppm | <0.001 ppm | <0.001 ppm |

TABLE 3

Quantity of silver ions in upstream portion of duct for circulation of fluids solution B

| | Time of use of the bottle | | | |
|---|---|---|---|---|
| | First use | 15 days | 30 days | 90 days |
| Volume of solution B extracted | 4 drops (0.15 ml) | 1.08 ml | 2.17 ml | 6.5 ml (approximately 200 drops) |
| In proximal portion of the insert (ppm) | 7.73 | 2.08 | 1.81 | 1.34 |
| In central portion of the insert (ppm) | 4.95 | 1.36 | 0.91 | 0.63 |
| In distal portion of the insert (ppm) | 1.08 | 0.36 | 0.42 | 0.27 |

TABLE 3-continued

Quantity of silver ions in upstream portion of duct for circulation of fluids solution B

| | Time of use of the bottle | | | |
|---|---|---|---|---|
| | First use | 15 days | 30 days | 90 days |
| In the reservoir (ppm) | <0.001 ppm | <0.001 ppm | <0.001 ppm | <0.001 ppm |

The results in these Tables 2 and 3 show on the one hand that silver ions are in fact retained in the insert and on the other hand that the quantity of silver ions retained in the insert diminishes from the proximal portion to the distal portion of the insert, whereas in the reserve of liquid the quantity of silver ions is below the detection threshold (0.001 ppm).

The reserve of liquid is thus well protected by the biocidal cations from chemical contamination.

The quantity of silver cations retained in the insert is large on first use, but it tends to diminish during prolonged use of the bottle, without however diminishing abruptly, which shows that a biocidal ion-exchange movement of takes place upstream of the membrane between the latter as a primary source of cations and the insert as a zone retaining biocidal cations conveyed by the back flow of liquid. The insert then becomes a secondary source of biocidal cations available to be used during withdrawals of liquid towards the membrane.

Forced Contamination Tests

Tests relating to the antimicrobial efficacy of the device by so-called forced tests of the antimicrobial efficacy over time are carried out on the one hand with a device D1 having an irradiated insert such as described with reference to the figures, with on the other hand a device D2 constituted like the device D1 except that the insert is not irradiated, in comparison with a device D3 the insert of which is made of irradiated polyethylene like the device D1, but the antimicrobial membrane of which is constituted by the same polymeric base material as that of the device of the invention but free of any biocidal agent.

The forced biological contamination test consists of simulating a use of the bottle by expulsion of drops of liquid followed by inoculation with contaminant germs in a given significant quantity, the quantity of germs being subsequently found in one drop of expelled solution then being determined. The test results shown hereinafter in Tables 4 and 5 were determined according to the following protocol. After a bottle containing a sterile solution had been brought into use by expulsion of four drops of this solution, a large quantity of contaminant germs, here $10^5$ (one hundred thousand) germs, were inoculated into the orifice in the tip of the bottle, then the quantity of germs present in one drop of liquid expelled 6 hours (time T6) after this first inoculation was determined. The next day, i.e. 24 hours after the bottle was brought into use, one drop of solution is extracted from the bottle, followed by an inoculation of $10^5$ germs into the tip of the bottle, this manipulation being carried out three times a day, once in the morning, once at midday and once in the evening, in order to simulate a usual use of eye drops. One drop of solution is extracted 24 hours (time T24) after the last inoculation and the quantity of germs present in this drop is determined.

On the other hand, forced contamination tests are carried out on similar bottles by first extracting drops of solution in a volume corresponding to three months' use of a given solution, then the forced contamination protocol is applied as above by inoculation of $10^5$ germs into the orifice in the tip and analysis of a drop of solution 6 hours later (at time T6), followed the next day by the manipulation for extraction of one drop followed by an inoculation, three times during the day, and the quantity of germs present in one drop extracted 24 hours (time 24) after this last inoculation is determined.

The bottles with the physiological solution A and the ophthalmic solution B that were previously described for the examples in Tables 2 and 3 are tested.

In these tests, two contaminant aerobic bacterial stains were used: a strain P of *Pseudomonas aeruginosa* and a strain E of *Escherichia coli*.

The results are shown in the following Tables 4 and 5:

TABLE 4 forced contamination tests with physiological solution A

| | Device D1 Insert irradiated | | Device D2 Insert not irradiated | | Device D3: No Ag cations in the membrane. | | Duration of use of the bottle |
|---|---|---|---|---|---|---|---|
| | T6 | T24 | T6 | T24 | T6 | T24 | |
| Strain P | 8 | 2 | 1,000 | 10 | 10,000 | 100,000 | Immediate |
| Strain P | <1 | <1 | 1,000 | 10 | 10,000 | 100,000 | At 3 months (10 ml extracted) |
| Strain E | 100 | <1 | 10,000 | 100 | 100,000 | 100,000 | Immediate |
| Strain E | 10 | <1 | 10,000 | 100 | 100,000 | 100,000 | At 3 months (10 ml extracted) |

TABLE 5 forced contamination tests with physiological solution B

| | Device D1 according to the invention | | Comparative device D2 with insert not irradiated | | Device D3 with membrane not initially loaded. | | Duration of use of the bottle |
|---|---|---|---|---|---|---|---|
| | T6 | T24 | T6 | T24 | T6 | T24 | |
| Strain P | <1 | <1 | 1,000 | 10 | 100,000 | 100,000 | Immediate |
| Strain P | <1 | <1 | 100 | 10 | 100,000 | 100,000 | At 3 months (6.5 ml extracted) |
| Strain E | <1 | <1 | 1,000 | 100 | 100,000 | 100,000 | Immediate |
| Strain E | <1 | <1 | 1,000 | 10 | 100,000 | 100,000 | At 3 months (6.5 ml extracted) |

The results of these Tables 4 and 5 show the high efficiency of the dispensing device according to the invention for maintaining the sterility of a liquid, sterile when placed in reserve, during a long usage through doses spaced out over time.

The results reported here have the benefit, when departing from the normal conditions of use of bottles for ophthalmic drops, of showing that the microbiological quality of the liquid delivered by means of the device of the invention remains acceptable, even when an exceptionally heavy contamination has been artificially caused. It follows that it is possible to use the same device of the invention in applications involving conditions that are much more severe in terms of risk of contamination, for example for products that are to be spread on wounds, burns, for atopical skin products in the cosmetics field, etc. Thus packaging such products in multidose bottles becomes possible thanks to the invention. In addition, it is clear that such results could not be hoped for with the previously known systems.

Tests with a Viscous Liquid

The forced contamination tests are carried out here in order to be suitable for a viscous solution, thanks to the use of a membrane with an average pore diameter markedly greater than 0.2 µm, chosen here by way of example as 0.8 µm, considerably greater than the porosity of 0.2 µm usually accepted for a good bacterial filtration efficiency.

A device according to the invention equipped with a membrane having an average pore diameter of 0.8 µm for use with a viscous solution V in comparison with a device according to the invention equipped with a membrane having an average pore diameter of 0.22 µm for use with a low-viscosity solution T is tested.

The two solutions are based on hyaluronic acid in different quantities, dissolved in water buffered to a pH of approximately 7. For a total volume of an aqueous solution of 100 ml, the viscous solution V contains 0.30 g of hyaluronic acid and has a viscosity of 60 mPa·s, whereas the low-viscosity solution T contains only 0.15 g of hyaluronic acid and has a viscosity of 3 mPa·s.

The forced contamination tests are carried out following the same protocol as previously described, and with the same two strains of contaminant germs, for an immediate use of the bottle and for a simulated use of 3 months. The results are shown in Table 6 hereinafter.

These tests prove a high level of efficiency of the dispensing device according to the invention in terms of biocidal effect over time, in maintaining the sterility of the liquid in the bottle despite a markedly lower antibacterial efficacy by filtration.

TABLE 6 contamination tests with the solutions T and V

| | Device according to the invention with 0.22 µm membrane and solution T | | Device according to the invention with 0.80 µm membrane and viscous solution T | | Duration of use of the bottle |
|---|---|---|---|---|---|
| | T6 | T24 | T6 | T24 | |
| Strain P | <1 | <1 | <1 | <1 | Immediate |
| Strain P | <1 | <1 | <1 | <1 | At 3 months (27 ml extracted) |
| Strain E | 2 | <1 | <1 | <1 | Immediate |
| Strain E | 2 | <1 | <1 | <1 | At 3 months (27 ml extracted) |

The above tests were carried out using a bottle equipped with a liquid dispensing head in which, according to the invention, the initial concentration of ionic load in the membrane, in silver cations, is of the order of several thousand ppm. Of course these are example cases, that can be adapted by modifying the estimated data depending on the conditions encountered in practice in each case of application of the invention.

Continuation of the Description of the Figures

According to a particular embodiment of the invention, the capillary channel is bored in a tip, itself produced from a material loaded with biocidal agent, here also supplied by an ion-supporting zeolite filler. The capillary channel 18 is thus produced in a tip of a dense polymeric material, not permeable by the liquid and air fluids, loaded with biocidal cations of silver that can be displaced by migrating from the mass to the surface. For example the tip can be made of polyethythene loaded with biocidal agent, in particular with zeolites supporting the silver cations.

A dispensing head the tip of which is thus loaded with biocidal agent whereas the material constituting the nacelle is devoid thereof is sufficiently described in the Applicant's prior patent WO2010/013131, making more detailed description thereof unnecessary here.

In order to complete the description of the device for dispensing liquid when applied to a bottle, with reference to FIGS. 3 and 4, it will be noted that upstream of the membrane in the wide part of the fluid-circulation duct provided by the annular shape of the nacelle 4, the free surface of the membrane is clear. However, supporting fins 16, 17 are formed on the nacelle, on the inside, to limit the stresses that could be exerted during operation on the periphery of the membrane where it is fixed bonded on a peripheral ring of the base of the tip provided with the capillary channel for expulsion of the liquid, but leaving the membrane free to curve away from the base 3 of the tip.

Opposite the external face of the membrane viewed with respect to its hydrophilic nature, the base 3 of the tip 5 forms a supporting surface for the membrane during the liquid-expulsion phases, which joins the wall of the capillary channel 18 at the level of its flared nozzle 28.

Around this nozzle, the free surface of the tip is scored with radial slots offering a wide cross-section for the passage of the liquid in proximity to the membrane on the outside of the bottle. The purpose of these radiating slots 31 is to collect the liquid leaving the bottle and guide it to the nozzle of the capillary channel 18 after it has passed through the membrane in its hydrophilic zone, but their role is also, with respect to the non-expelled remaining liquid that is aspirated back to the bottle in the air-entry phase compensating for the expelled liquid, to facilitate its being directed, under the pressure of the air to the hydrophilic zone 22, freeing the central hydrophobic zone 23 for the air that then arrives above.

Furthermore, the surface of the base 3 has corrugations that tend to finely divide any path for the circulation of air arising at the outlet of the nozzle of the capillary channel of the tip, which tends to reduce the speed at which it then crosses the membrane, even when the latter is pushed away from the transversal surface of the base of the tip.

In the preferred embodiment of a tip thus produced according to the invention, in particular in the case of a dropper tip, the corrugations dividing any air circulation path are present in the form of grooves 32, which are relatively narrow and not very deep, thus having a fine flow section, which are each annular and distributed in a concentric arrangement with respect to one another around the central capillary channel of the tip. These grooves 32 are cut into the surface of the base of the tip, in the sectors of the base retained by the slots 31 for guiding the flow of liquid, at the point where the surface of the base of the tip is rather reserved to act as a bearing support for the membrane when the latter is pushed by the internal pressure of the compressed bottle in order to expel liquid.

It is understood that during operation, the particular configuration of the surface of the tip facing the membrane plays a role in the organization of the circulation of the fluids, not only by promoting an alternation between liquid flow and gaseous flow in the central channel of the tip, but also by guiding the fluids on their return path as shown by the arrows in FIG. 4. The arrows f1 show that the non-expelled remaining liquid that is returned first is diverted from a direct axial path and oriented towards the hydrophilic part of the membrane 22. It is thus prevented from being sprayed onto the central part of the membrane, where it would tend to wet the material of the membrane, which has a hydrophobic character in this area. The flow of aspirated air towards the bottle thereby has free access to the hydrophobic material of the membrane in its central portion 23, as shown by the arrows f2.

Returning now to FIG. 1, together with FIG. 2, it is possible to observer other details of the realization of the head for dispensing liquid from a sterile packaging bottle which, while themselves being standard features of the bottles manufactured industrially by the Applicant, are nonetheless means involved in the implementation of the present invention due to their property of maintaining sterility in the bottle.

In this respect, the presence of external peripheral ribs 15 on the nacelle 4, which ensure sealing against bacteria with the neck of the bottle 10 at the level of the porous insert 8 will be noted. The configuration of the cap 6 will also be noted, which is such that, when it is screwed (at 12) onto the neck of the bottle, it closes the external nozzle of the channel 18. Among other things, its role is to ensure a pressure drop downstream of the membrane that prevents the latter being wetted by the liquid contained in the bottle provided that the tamper-proof ring 26 has not been broken for a first use (first expulsion of a drop of liquid).

Similarly, the shape of the nacelle 8 at its upstream end, inside the bottle, will also be noted. Its utility will become apparent firstly, in embodiments intended for dispensing eye drops with surface-active or viscous physico-chemical features, and in such cases the means shown will advantageously be exploited in combination with more specific embodiments of the invention, namely those providing for a membrane having a relatively coarse porosity leading to lower protection from microorganisms by filtration, while protection by biocidal effect is high. These means reside in the configuration forming arches 13 around a central pad 11 and being arranged in the bottle 2 beyond its neck 10. These have been fully described in patent application WO 2011/095877. They contribute to an organization of the circulation of the fluids that is favourable to the requirements of the present invention in the case of the same liquids.

The test results reported above demonstrate an improvement in microbiological safety throughout the duration and under exposure to significant contaminants, which could not be expected simply from using a membrane loaded with biocidal cations. Nor could they be expected from such a membrane, which would also be partially hydrophilic and hydrophobic, inasmuch as such a membrane could not on its own ensure alternation of the flows of liquid and air which circulate from the bottle to the outside and vice versa.

In the case of the invention, this alternate circulation is ensured by the fact that the partially hydrophilic and partially hydrophobic membrane forming the interface between the inside and the outside of the bottle is combined with a capillary channel for the expulsion of liquid and entry of air situated downstream of the membrane. It is also further ensured by the other means which contribute in a known manner to managing the alternation of the flows under the effects of pressure, and thereby to the regularity and the reproducibility of the masses and volumes conveyed.

Finally, although the fact of applying the membrane loaded with biocidal ions in a conventional bottle by the Applicant is already inventive owing to the role that it is made to play in the transport of the active load on the back flow of the liquid created at each operation of dispensing a dose of liquid, nevertheless it would still not be possible to obtain the results demonstrated without adding the presence of an insert, made porous in order to act as a non-sealing closure stopper of the bottle, and if applicable, regulating the flow by its porous character as is conventionally the case, but which moreover is constituted by a polymeric material with anionic sites in its mass, having the effect of attracting metal cations that carboxylic sites in particular may have.

Differences of behaviour in the ionic transfers can in fact be explained by considering that the membrane is a finely porous component having a relatively large extent across the duct for the circulation of the fluids and having a small thickness, whereas for its part, the insert has a relatively coarse porosity and it is thick, thus having a relatively great length along the circuit for the circulation of the fluids. Also considering that unlike the capillary channel on the downstream side, this insert occupies the neck of the bottle over a relatively extensive cross-section, like the membrane.

Moreover, whereas in the membrane the individual cells of the material are scarcely filled, whether by liquid or air, it will be observed that in the insert the two fluids are present simultaneously within the cells. Therefore, the oxygen in the air can have an effect on the transfers of ionic loads within the cells. The biocidal activity in the destruction of the aerobic bacteria is thus exerted there differently than in the cells of the membrane. In addition, air and liquid come into contact with a large surface area of active material, corresponding with the specific surface of the insert. This makes the use of the cationic loads in the destruction of the bacteria more effective.

Clearly, a similar effect cannot take place at the level of the circuit situated downstream of the membrane since there, the material of the tip is dense and impermeable both to the liquid and to the air. Consequently, even if this material is based on an ionic polymer initially bearing silver ions, these ions must migrate to the surface in order to be active on the fluids. The surface of contact with the fluids at the level of the tip is long, but its perimeter around the section of the capillary channel is small. Moreover, it is alternately in the presence of either air or water, including during the back flow of the remaining aqueous solution that has not been expelled.

The phenomena involving the transfers of the ionic loads between the bi-functional interface membrane and the porous insert capping the bottle are all the more clearly differentiated as the organization of the circulation of the fluids through them is better controlled in order to ensure that the membrane remains dry in its hydrophobic zone and that the back flow of liquid passes through its hydrophilic zone. While the bottle is in storage, before the first use consuming the liquid, the membrane remains dry regardless of the position of the bottle, thanks to an overpressure ensured on the downstream side by the sealed closure of the capillary channel; this overpressure also obtains upstream, so as to keep the membrane isolated from any contact with the porous insert.

In any event, it is a fact that between the two porous bodies, being the membrane and the porous insert, during operation a bed is created, of mobile ions that are removed from the insert by the flow of liquid extracted from the bottle at each dispensing operation, from biocidal ions that have been brought there by a back flow of liquid not dispensed during the preceding liquid dispensing operations. In practice, the biocidal ions thus remain confined to movements from one to the other of the porous bodies. Downstream of the membrane, the expelled liquid is not affected.

Without claiming to fully understand the phenomena that occur on the scale of the molecules and of the ionic loads, it is possible to envisage a mechanism involving the availability of the directly accessible active sites for contact with the fluids at the surface of the polymeric material, given the large specific surface area and of the large pore volume at the level of the insert and given the small thickness of the membrane. The membrane constitutes a primary source that would have been sufficiently loaded with biocidal agent during manufacture to be capable of generously supplying the quantity of ions required in order to satisfy the requirements of each application throughout the lifetime of the bottle until its initial liquid content is exhausted. For its part, during manufacture the insert is crucial as the source of active charged sites additional to that of the biocidal ions. From the time when the bottle has been opened for a first dispensing operation, the insert plugging the bottle enters into operation both in order to protect the sterile inner space and in order to constitute a secondary source of biocidal agent, which keeps in reserve the ions that have been brought there at the end of a dispensing operation (air aspiration phase), until they are taken up during a subsequent dispensing operation. Those which will thus be taken up by the flow of liquid removed from the bottle will be conveyed as far as the membrane and will be retained there, with the exception however of those which will have been consumed on the way by bacteria present in the air.

The high quality of the sterility maintenance noted during the forced contamination tests goes far beyond the specific requirements in the case of bottles for eye drops and other ophthalmic liquids, that it has become customary to store under the protection of membranes filtering out the external microorganisms. Conversely, it shows that the technology of the invention retains its benefit as an alternative to the conventional methods even in this case, whereas generally it will be useful in many applications that do not require, or do not allow, fine bacterial filtration at the level of the membrane. Also, it is easily understood that the invention can be specifically implemented in embodiments suitable for large liquid capacities and long lifetimes in the case of discontinuous use and/or doses and forms of dispensing that are very diverse for the liquid expelled from the channel for alternate circulation of the fluids, by simple dimensional adaptations of the essential constituent elements of the device according to the invention.

The invention claimed is:

1. A device capable of dispensing an aqueous liquid, by doses spaced out over time, comprising a closed upstream space accommodating a liquid, an open downstream space via a capillary channel opening to ambient air, a partially hydrophilic and partially hydrophobic interface membrane, whereby, in operation, during each time a dose of liquid is dispensed, the flows of air and of liquid circulate alternately in the capillary channel and a back flow of non-expelled remaining liquid takes place, said interface membrane (7) being a filtration material the mass of which comprises biocidal metal cations, said device further comprising a porous insert (8), permeable both to liquid and to air, which is arranged upstream of the membrane on the path of the fluids and which is made of a material containing negatively charged sites capable of attracting biocidal metal cations originating from said membrane, and wherein the porous insert progressively collects the biocidal metal cations originating from said membrane present in the back flow of non-expelled remaining liquid, such that liquid accommodated in the closed upstream space remains free of biocidal cations, so that to-and-fro movements of biocidal cations are established, conveyed by flow of liquid outward and back flow of liquid in return direction between the membrane and the porous insert, providing biocidal activity in the device for dispensing liquid, thus protecting the liquid accommodated in the closed upstream space from microbiological contamination.

2. The device according to claim 1, wherein said biocidal metal cations comprise silver cations.

3. The device according to claim 1, wherein said biocidal metal cations of the membrane are supported by mineral macromolecules incorporated in the mass of the base material of the membrane.

4. The device according to claim 1, wherein said negatively charged sites capable of attracting biocidal metal cations are anionic carboxyl groups.

5. The device according to claim 1, wherein said porous insert has a volumetric mass density of 0.2 to 0.8 $g.cm^3$.

6. The device according to claim 1, wherein said insert is based on a polyolefin polymer.

7. The device according to claim 1, wherein said insert is constituted by a compacted fibrous material.

8. The device according to claim 1, wherein said negatively charged sites capable of attracting biocidal metal cations result from irradiation of the porous insert with rays of the beta or gamma type in the presence of oxygen.

9. The device according to claim 1, wherein the material constituting said membrane has a pore diameter of 0.1 to 1 μm.

10. The device according to claim 1, wherein the material constituting said membrane has an average pore diameter of 0.4 to 0.8 μm.

11. The device according to claim 1, wherein said capillary channel is formed within a material incorporating biocidal metal cations.

12. A sterile packaging bottle capable of dispensing an aqueous liquid in doses spaced out over time, by expulsion of a dose of liquid out of the bottle and entry of outside air in compensation, said sterile packaging bottle comprising a device dispensing said liquid according to claim 1, said insert (8) of which is mounted as a non-sealing closure of the inside of the bottle, said closed space then being inside the bottle.

13. The bottle according to claim 12, having a wall that can be reversibly elastically deformed, in order to ensure the entry of outside air compensating for any dose of liquid expelled from the bottle as well as the back flow through said device of any non-expelled remaining liquid, said membrane being mounted with said porous insert (8) in said device for dispensing liquid in combination with means of organization of the circulation of the air and liquid fluids through it, and in which said membrane is arranged at the base of a dropper tip within which is arranged the capillary channel (18) for the expulsion of the drops, opposite a base of said tip in which are arranged respective means for guiding the air aspired from the outside and any remaining liquid that has not been dispensed and is required to flow back to the downstream portion of the duct for the circulation of the fluids, which tend to direct the airflow to the hydrophobic part of the membrane and to distribute the liquid over its hydrophilic part.

14. The bottle according to claim 12, in which said insert participates in the organization of the circulation of the fluids by constituting a flow regulator.

15. The device according to claim 6, wherein the polyolefin polymer is polyethylene, polypropylene, or a copolymer of ethylene or of polypropylene with up to 25% higher homologs of carboxylic acids or esters.

16. The device according to claim 11, wherein said capillary channel is formed within a material incorporating biocidal metal cations borne by mineral macromolecules.

17. The bottle according to claim 13, wherein the means for guiding the air aspired from the outside and any remaining liquid that has not been dispensed and is required to flow back to the downstream portion of the duct for the circulation of the fluids, which tend to direct the airflow to the hydrophobic part of the membrane are arranged in the center of said membrane.

* * * * *